United States Patent

Honda et al.

[11] Patent Number: 5,556,897
[45] Date of Patent: Sep. 17, 1996

[54] PRIMER SOLUTION COMPOSITIONS AND METHOD OF FORMING ADHESIVE LAYER ON TOOTH SURFACE

[75] Inventors: Narimichi Honda, Shiga-ken; Takashi Yamamoto; Masami Arata, both of Moriyama, all of Japan

[73] Assignee: Sun Medical Co., Ltd., Moriyama, Japan

[21] Appl. No.: 361,709

[22] Filed: Dec. 22, 1994

Related U.S. Application Data

[63] Continuation of Ser. No. 86,992, Jul. 7, 1993, abandoned.

[30] Foreign Application Priority Data

Jul. 10, 1992 [JP] Japan .................................. 4-206267

[51] Int. Cl.⁶ ............................................ A61K 6/08
[52] U.S. Cl. .................... 523/118; 433/228.1; 156/327
[58] Field of Search ........................ 424/78.8; 424/78.8, 424/78.2; 523/118; 156/327, 33.1; 433/228.1

[56] References Cited

U.S. PATENT DOCUMENTS

| | | | |
|---|---|---|---|
| 4,259,117 | 3/1981 | Yamauchi et al. | 526/277 |
| 4,446,246 | 5/1984 | Mc Ginniss | 502/155 |
| 4,731,146 | 3/1988 | Clark | 526/240 |
| 4,985,516 | 1/1991 | Sakashita et al. | 526/196 |

*Primary Examiner*—Peter F. Kulkosky
*Attorney, Agent, or Firm*—Sherman and Shalloway

[57] ABSTRACT

A primer solution composition to be applied to a tooth surface, which comprises (a) at least one metal compound selected from the group consisting of an iron compound, a copper compound and a cobalt compound, (b) a polymerizable monomer having an acidic group and (c) a polymerizable monomer having no acidic group, and which has adhesion properties to a tooth surface; and a method of forming an adhesive layer on a tooth surface, which comprises applying said primer solution composition comprising (a) to a tooth surface, and applying thereto a curing composition containing trialkylboron or its partial oxidate and a polymerizable monomer.

21 Claims, 1 Drawing Sheet

PRIMER SOLUTION COMPOSITIONS AND METHOD OF FORMING ADHESIVE LAYER ON TOOTH SURFACE

This application is a continuation of application Ser. No. 08/086,992, filed Jul. 7, 1993, now abandoned.

DETAILED DESCRIPTION OF THE INVENTION

Figure 1:
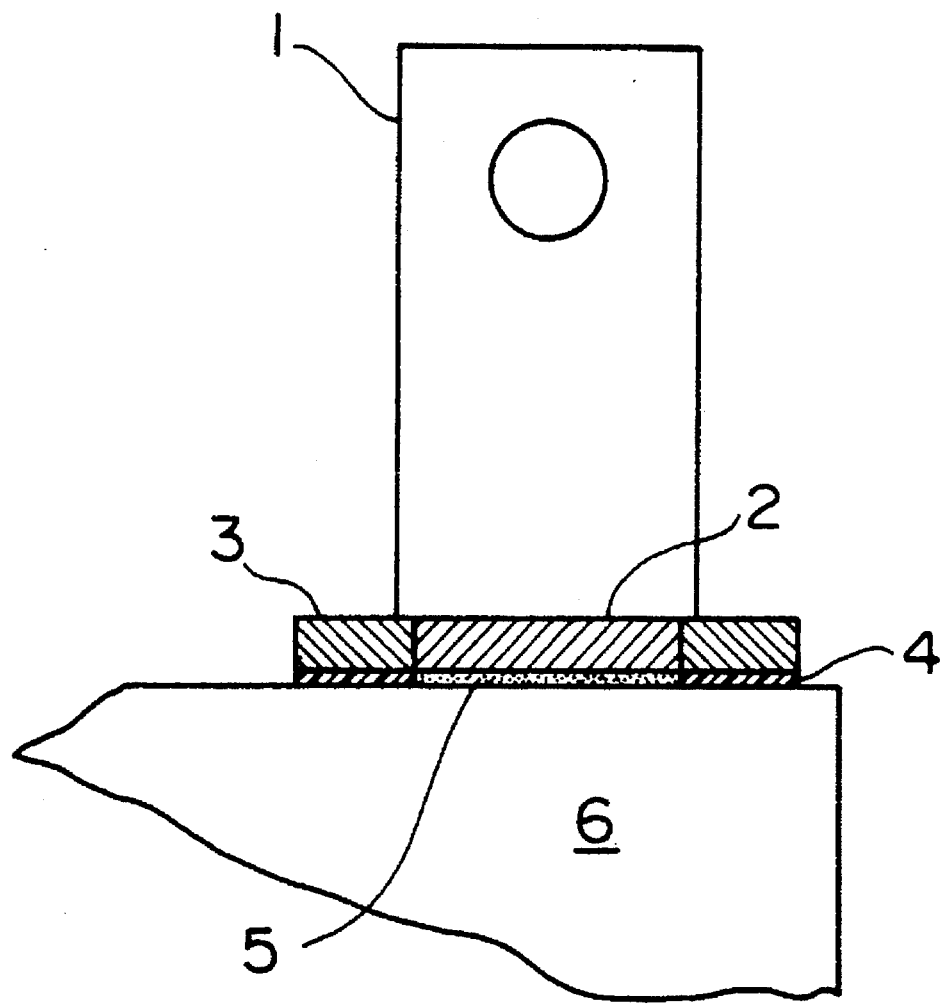

The present invention relates to a primer solution composition and a method of forming an adhesive layer on a tooth surface by consecutively applying the primer solution composition and a curing composition on the tooth surface.

In the field of dental therapy, it is required to bond a tooth, particularly dentin, and a material for restoring the tooth such as a polymer material, a metal or a ceramic material to each other strongly, and a variety of adhesives for this purpose have been already proposed.

The so far proposed adhesives generally have a three component system consisting of (1) a polymerizable monomer, (2) a polymerization catalyst or a polymerization initiator and (3) a filler.

Typical examples of the above adhesives include the following:

an adhesive composition containing (1) (meth)acrylate ester as a polymerizable monomer, (2) a mixture of benzoyl peroxide and an aromatic tertiary amine or a mixture of benzoyl peroxide, an aromatic tertiary amine and a sulfinic acid salt as a polymerization catalyst and (3) a filler such as a polymer and silica;

an adhesive composition containing (1) (meth)acrylate ester as a polymerizable monomer, (2) a photopolymerization initiator consisting of camphorquinone as a photosensitizer and N,N-dimethylaminoethyl methacrylate as a reducing agent and (3) a filler such as a polymer and silica; and an adhesive composition containing (1) (meth)acrylate ester as a polymerizable monomer, (2) a partial oxidate of tributylboron (TBBO) as a polymerization catalyst and (3) a filler such as a polymer and silica.

In the above known adhesive compositions, a variety of compounds are used as polymerization initiators for polymerizable monomers. Further, for improving these adhesives in adhesion properties, it has been proposed to use an adhesion-promoting monomer or a monomer having affinity to a tooth. As this adhesion-promoting monomer or a monomer having affinity to a tooth, for example, there are known monomers having a carboxyl group (or a group convertible to a carboxyl group) such as 4-methacryloyloxyethyltrimellitic acid (4-MET) or its anhydride (4-META) and 10-methacryloyloxydecylmalonic acid (MAC-10) and monomers having phosphoric acid group such as 10-methacryloyloxydecyldihydrogen phosphate.

A tooth includes enamel and dentin. The enamel is almost composed of hydroxyapatite. When the enamel surface is etched with phosphoric acid and the above adhesive is applied thereonto, practically sufficient adhesion strength and adhesion durability can be obtained.

As for the dentin, when it is etched with a citric acid solution containing ferric chloride and an adhesive containing TBBO as a polymerization initiator is applied, high adhesion strength is exhibited. In many cases, however, other adhesives fall to show sufficient adhesion strength to the dentin.

In the above prior techniques, the adhesive containing TBBO is the most excellent, but it is required to pretreat a tooth to obtain excellent adhesion strength with this adhesive. That is, it is recommended to use TBBO as a polymerization initiator and etch a tooth with a 10% citric acid aqueous solution containing 3% ferric chloride for 30 seconds (this treatment is generally called "10-3 treatment"). This 10-3 treatment is highly useful for increasing adhesion strength to the dentin. However, this treatment requires removal of an acid by full washing since it is acid treatment. Further, the dentin may be injured more than necessary, and it has been pointed out that the adhesive might peel off from an injured portion of the dentin in a long period of time after the application of the adhesive.

The following problem has been also pointed out. Due to the "10-3 treatment", dentin tubules open, and stimuli from an adhesion site (pressure, a temperature change and chemical substances such as a monomer) directly reach the dental pulp, causing a strong toothache on a patient.

It is an object of the present invention to provide a primer solution composition to be applied to a tooth surface.

It is another object of the present invention to provide a primer solution composition which exhibits high adhesion strength without injuring a dentin.

It is further another object of the present invention to provide a method of forming an adhesive layer on a tooth surface by consecutively applying the primer solution composition of the present invention and a curing composition to the tooth surface.

Other objects and advantages of the present invention will be apparent from the following description.

According to the present invention, the above objects and advantages of the present invention are achieved, first, by a primer solution composition to be applied to a tooth surface.

(A) which comprises (a) at least one metal compound selected from the group consisting of an iron compound, a copper compound and a cobalt compound, (b) a polymerizable monomer having an acidic group and (c) a polymerizable monomer having no acidic group, and (B) which has adhesion properties to a tooth surface.

FIG. 1 is a schematic view showing a sample for an adhesion test.

In the present invention, the above metal compound (a) is selected from an iron compound, a copper compound and a cobalt compound. Specific examples thereof preferably are halides such as chlorides and fluorides of the above metals; inorganic acid salts such as nitrates and sulfates of the above metals; organic acid salts such as acetates, acrylates, methacrylates and other salts of the above metals; and organic complexes of the above metals such as a complex of acetylacetone with any one of the above metals. These metal compounds may have a valence of any value.

Examples of the iron compound include salts of inorganic acids such as iron chloride, iron nitrate and iron sulfate, salts of organic acids such as iron acrylate and iron methacrylate, and complex salts such as iron acetylacetonate.

Examples of the copper compound include salts of inorganic acids such as copper chloride, copper fluoride, copper nitrate and copper sulfate, salts of organic acids such as copper acetate, copper acrylate and copper methacrylate, and complex salts such as copper acetylacetonate.

Examples of the cobalt compound include salts of inorganic acids such as cobalt chloride, cobalt nitrate and cobalt sulfate, salts of organic acids such as cobalt acetate, cobalt acrylate and cobalt methacrylate, and complex salts such as cobalt acetylactonate.

The above metal compounds may be used alone or in combination. The content of the metal compound in the primer is preferably 0.0001 to 1% by weight.

The primer solution composition of the present invention contains (b) a polymerizable monomer having an acidic group. The polymerizable monomer having an acidic group is preferably selected, for example, from monomers having a carboxylic acid group or its acid anhydride group, monomers having a phosphoric acid group and monomers having a sulfonic acid group.

Examples of the monomers having a carboxylic acid group or its acid anhydride group include (meth)acrylic acid and its acid anhydride, 1,4-di(meth)acryloxyethylpyromellitic acid, 6-(meth)-acryloxyethylnaphthalene- 1,2,6-tricarboxylic acid, N-(meth)acryloyl-p-aminobenzoic acid, N-(meth)acryloyl-o-aminobenzoic acid, N-(meth)acryloyl-m-aminobenzoic acid, N-(meth)acryloyl-5-aminosalicylic acid, N-(meth)acryloyl- 4-aminosalicylic acid, 4-(meth)acryloxy ethyltrimellitic acid and its acid anhydride, 4-(meth)acryloxybutyltrimellitic acid and its acid anhydride, 4-(meth)acryloxyhexyltrimellitic acid and its acid anhydride, 4-(meth)acryloxydecyltrimellitic acid and its acid anhydride, 2-(meth)acryloyloxybenzoic acid, 3-(meth)acryloyloxybenzoic acid, 4-(meth)acryloyloxybenzoic acid, β-(meth)acryloyl oxyethylhydrogensuccinate, β-(meth)acryloyl oxyethylhydrogenmaleate, β-(meth)acryloyl oxyethylhydrogenphthalate, 11-(meth)acryloyloxy-1,1-undecanedicarboxylic acid and p-vinylbenzoic acid.

Examples of the monomers having a phosphoric acid group include (2-(meth)acryloxyethyl)phosphoric acid, (2-(meth)acryloxyethylphenyl)phosphoric acid and 10-(meth)acryloxydecylphosphoric acid.

Examples of the monomers having a sulfonic acid group include p-styrenesulfonic acid and 2 -acrylamide-2-methylpropanesulfonic acid.

The above monomers having an acidic group (b) may be used alone or in combination.

Of the above monomers, N-(meth)acryloyl-5-aminosalicylic acid, N-(meth)acryloyl-4-aminosalicylic acid and 4-(meth)acryloxyethyltrimellitic acid and its acid anhydride are particularly advantageously used.

The content of the acidic monomer in the primer is preferably 0.1 to 30% by weight.

The primer solution composition of the present invention further contains (c) a polymerizable monomer having no acidic group.

The above polymerizable monomer (c) is preferably selected from monofunctional or polyfunctional compounds having no acidic group but having a radical-polymerizable double bond in the structure.

Examples of the monofunctional polymerizable monomers having no acidic group include hydrocarbon esters of (meth)acrylic acid such as methyl (meth)acrylate, ethyl (meth)acrylate, butyl (meth)acrylate, hexyl (meth)acrylate, 2-ethylhexyl (meth)acrylate, dodecyl (meth)acrylate, lauryl (meth)acrylate, cyclohexyl (meth)acrylate, benzyl (meth)acrylate, isobornyl (meth)acrylate and adamantyl (meth)acrylate; hydroxyalkyl esters of (meth)acrylic acid such as 2-hydroxyethyl (meth)acrylate, 2-hydroxypropyl (meth)acrylate, 1,2- or 1,3-dihydroxypropyl mono(meth)acrylate, 2-hydroxypropyl- 1,3-di(meth)acrylate, 3-hydroxypropyl-1, 2-di(meth)acrylate, erythritol mono(meth)acrylate, erythritol di(meth)acrylate and erythritol tri(meth)acrylate; N-hydroxyalkyl (meth)acrylamides such as N-methylol (meth)acrylamide; polyglycol mono(meth)acrylates such as diethylene glycol mono(meth)acrylate, triethylene glycol mono(meth)acrylate, polyethylene glycol mono(meth)acrylate and polypropylene glycol mono(meth)acrylate; (poly)glycol monoalkyl ether (meth)acrylates such as ethylene glycol monomethyl ether (meth)acrylate, ethylene glycol monoethyl ether (meth)acrylate, ethylene glycol monododecyl ether (meth)acrylate, diethylene glycol monomethyl ether (meth)acrylate, triethylene glycol monomethyl ether (meth)acrylate, polyethylene glycol monomethyl ether (meth)acrylate and polypropylene glycol monoalkyl ether (meth)acrylate; fluoroalkyl esters of (meth)acrylic acid such as perfluorooctyl (meth)acrylate and hexafulorobutyl (meth)acrylate; silane compounds having a (meth)acryloxyalkyl group such as γ-(meth)acryloxypropyltrimethoxysilane and γ-(meth)acryloxypropyltri(trimethylsiloxy)silane; and (meth)acrylates having a heterocylic ring such as tetrafurfuryl (meth)acrylate.

Examples of the polyfunctional polymerizable monomers having no acidic group include poly(meth)acrylates of alkane polyol such as ethylene glycol di(meth)acrylate, propylene glycol di(meth)acrylate, butylene glycol (meth)acrylate, neopentyl glycol di(meth)acrylate, hexylene glycol di(meth)acrylate, trimethylolpropane tri(meth)acrylate, glycerin tri(meth)acrylate and pentaerythritol tetra(meth)acrylate; poly(meth)acrylates of polyoxyalkane polyol such as diethylene glycol di(meth)acrylate, triethylene glycol di(meth)acrylate, polyethylene glycol di(meth)acrylate, dipropylene glycol di(meth)acrylate, polypropylene glycol di(meth)acrylate, dibutylene glycol di(meth)acrylate and dipentaerythritol hexa(meth)acrylate; epoxy (meth)acrylates of the formula (1),

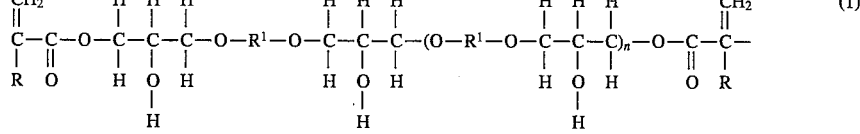

(1)

wherein R is a hydrogen atom or a methyl group, n is 0 or a positive integer and each of $R^1$s is —$(CH_2)_2$—, —$(CH_2)_4$—,

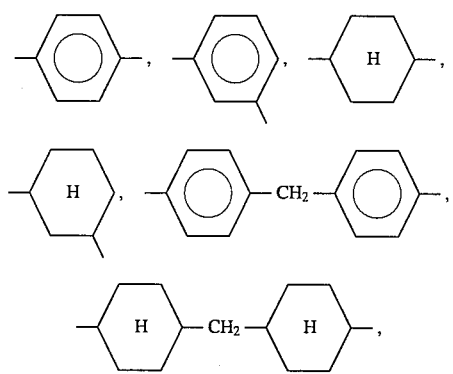

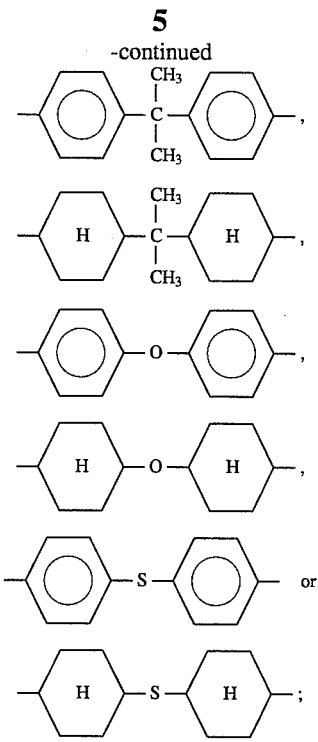

alicyclic or aromatic di(meth)acrylates of the formula (2),

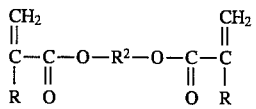

wherein R is as defined in the above formula (1), and $R^2$ is

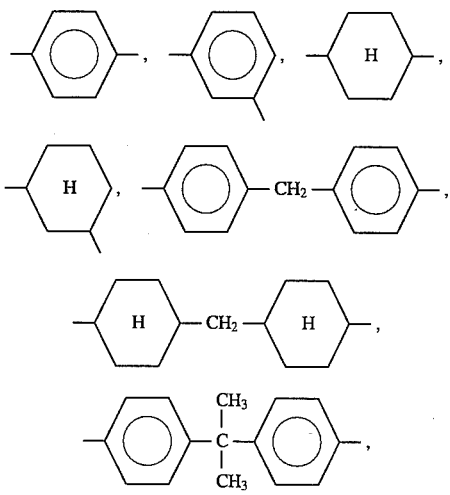

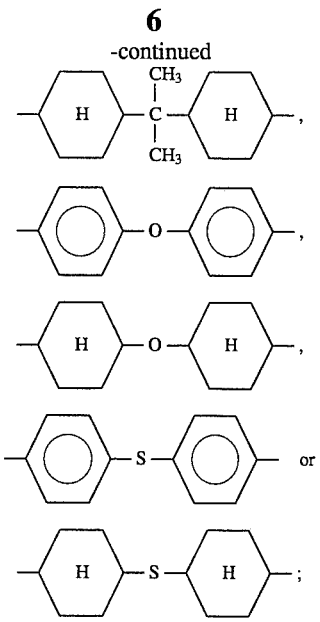

alicyclic or aromatic di(meth)acrylates of the formula (3),

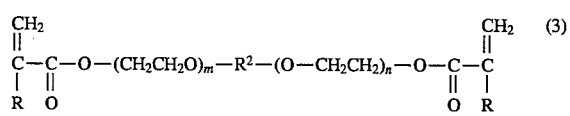

wherein R is as defined in the above formula (1), each of m and n is a positive integer and $R^2$ is as defined in the above formula (1).

Further, example of the above monomers include polyfunctional (meth)acrylates having at least one urethane bond in the molecule such as an adduct of 1 mol of a diisocyanate compound with 2 mol of a hydroxyl group-containing (meth)acrylate such as 2-hydroxyethyl (meth)acrylate. The diisocyanate compound can be selected from aliphatic, alicyclic and aromatic diisocyanates. Examples of the diisocyanate compound include hexamethylene diisocyanate, lysine diisocyanate, 2,2,4- or 2,4,4-trimethylhexamethylene diisocyanate, bisphenol A diisocyanate, dicyclohexyldimethylmethane diisocyanate, isophorone diisocyanate, tolylene diisocyanate, xylylene diisocyanate, diphenylmethane diisocyanate and thalene amples of the polyfunctional (meth)acrylate having at least one urethane bond in the molecule include compounds of the formula (4),

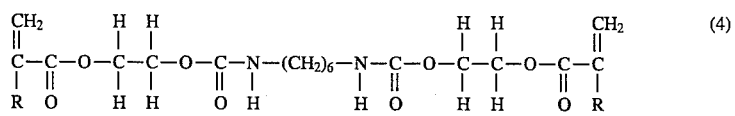

wherein R is as defined in the above formula (1), compounds of the formula (5),

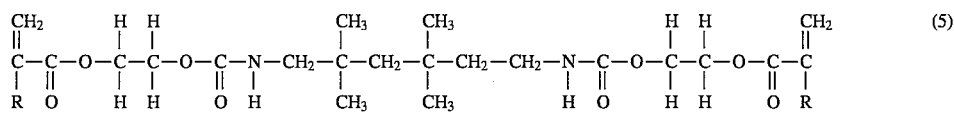

wherein R is as defined in the above formula (1), compounds of the formula (6),

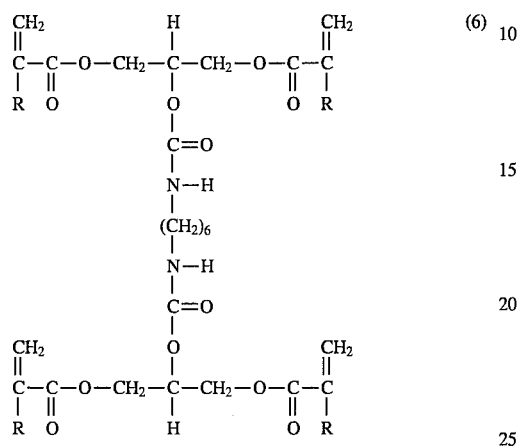

wherein R is as defined in the above formula (1), compounds of the formula (7)

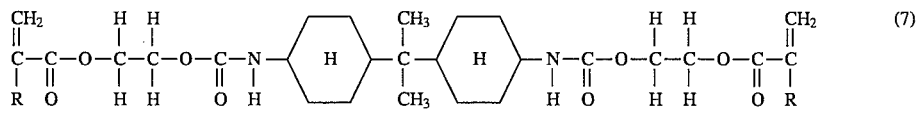

wherein R is as defined in the above formula (1), compounds of the formula (8),

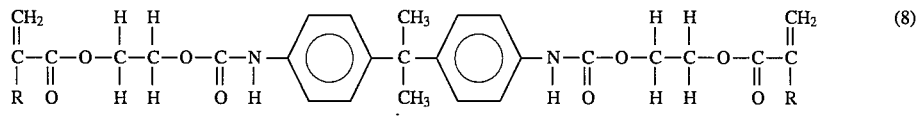

wherein R is as defined in the above formula (1), compounds of the formula (9),

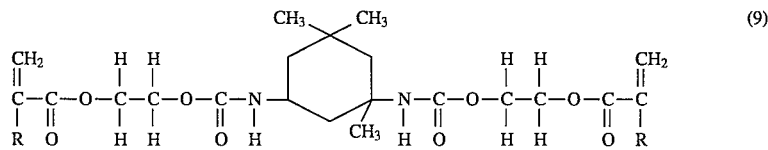

wherein R is as defined in the above formula (1), compounds of the formula (10),

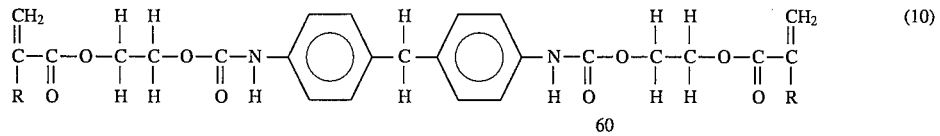

wherein R is as defined in the above formula (1), and compounds of the formula (11),

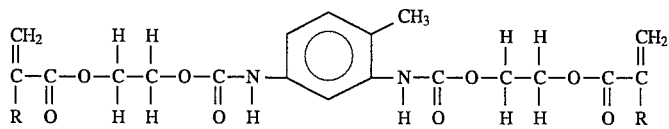

(11)

wherein R is as defined in the above formula (1).

As the above monofunctional polymerizable monomers, particularly preferred are alkyl (meth)acrylates such as methyl (meth)acrylate, ethyl (meth)acrylate and 2-ethylhexyl (meth)acrylate; hydroxyl group-containing (meth)acrylates such as 2-hydroxyethyl (meth)acrylate, 2-hydroxypropyl (meth)acrylate, 2-hydroxypropyl-1,3-di(meth)acrylate, 1,3-dihydroxypropyl mono(meth)acrylate and erythritol mono(meth)acrylate; and (meth)acrylates having an ethylene glycol chain in the molecule such as triethylene glycol monomethyl ether mono(meth)acrylate and triethylene glycol mono(meth)acrylate.

As the above polyfunctional polymerizable monomers, particularly preferred are di(meth)acrylates having an ethylene glycol chain in the molecule such as triethylene glycol di(meth)acrylate and polyethylene glycol di(meth)acrylate, compounds of the formula (1)-1,

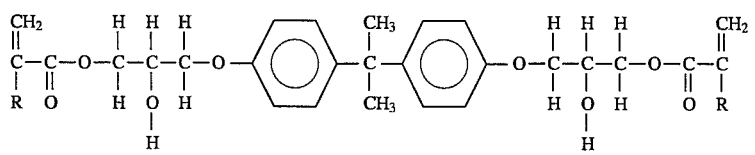

wherein R is as defined in the above formula (1), compounds of the above formula (5), compounds of the formula (3)-1,

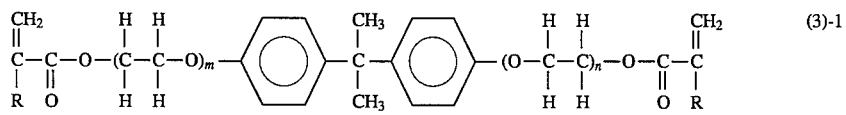

wherein R is as defined in the above formula (1) and m+n equals 2 to 20,
and compounds of the formula (3-2),

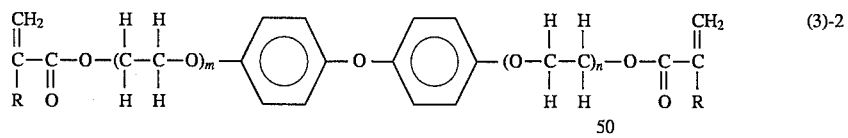

wherein R is as defined in the above formula (1) and m+n equals 2 to 20.

The above monomers may be used alone or in combination.

The content of the (c) polymerizable monomer having no acidic group in the primer is preferably 70 to 99.9% by weight.

The percent by weight amounts of the metal compound (a), the polymerizable monomer having an acidic group (b) and the polymerizable monomer having no acidic group (c) are based on the weight of the components (a), (b), and (c) in the primer composition.

The above-specified (a) metal compound, (b) polymerizable monomer having an acidic group and (c) polymerizable monomer having no acidic group are dissolved or dispersed in a solvent before use. The solvent works to adjust the viscosity of the solution or dispersion and improve the coatability thereof. The solvent is freely selected from solvents which are non-toxic to a human body, such as water, ethanol, isopropanol, acetone and tetrahydrofuran. These solvents may be used alone or in combination. The content of the solvent in the primer is 5 to 95% by weight, preferably 30 to 80% by weight.

The weight percent of solvent is based on the weight of the components (a), (b), (c) and the solvent (d).

The primer composition of the present invention characteristically has adhesion property to a tooth surface.

The primer composition of the present invention is therefore applied to a tooth surface. For example, the primer composition of the present invention is applied and dried, and then a curing composition is applied thereto to form an adhesive layer. Thus, a material selected from various materials can be bonded to a tooth through the adhesive layer. In this case, after the application of the curing composition and before the curing of this composition, a filler or a remedying material may be placed thereon as required to bond the same to a tooth by means of the adhesion strength of this curing agent.

The curing composition can be selected from a variety of curing compositions known in the field of this art. Above all, preferred is a curing composition containing trialkylboron.

According to the present invention, therefore, there is further provided a method of forming an adhesive layer on a tooth surface, which comprises applying the primer solution composition of the present invention to a tooth surface and then applying a curing composition containing trialkylboron or its partial oxidate and a polymerizable monomer thereonto.

As described above, the curing composition to be applied onto the primer contains trialkylboron such as tributylboron (TBB) or its partial oxidate (TBBO) and a polymerizable monomer. As the polymerizable monomer, preferred are (meth)acryloyl monomers. Examples of the (meth)acryloyl monomers include monofunctional (meth)acrylates such as methyl (meth)acrylate, ethyl (meth)acrylate, hexyl (meth- )acrylate, tetrahydrofurfuryl (meth)acrylate and 2-hydroxyethyl (meth)acrylate; difunctional (meth)acrylates such as ethylene glycol di(meth)acrylate, triethylene glycol di(meth)acrylate and hexamethylene glycol di(meth)acrylate; (meth)acrylates having at least three functional groups such as trimethylolpropane tri(meth)acrylate and pentaerythritol tetra(meth)acrylate; 4-methacryloyloxyethoxycarbonylphthalic acid and its acid anhydride; and (meth)acryloyl compounds having an acidic group such as 5-methacrylaminosalicylic acid and 10-methcryloyloxydecyldihydrogenphosphate. The above curing composition may contain other component such as a polymethyl methacrylate powder in such an amount that the adhesive properties of the composition of the present invention is not impaired. That is, this curing composition may be used either as an adhesive for bonding a filler such as a metal or as a liner for a composite resin.

According to the present invention, high bond strength between a dentin and a variety of materials can be obtained without treating the dentin with an acid.

The present invention will be further explained hereinafter by reference to Examples. However, the present invention shall not be limited to these Examples.

EXAMPLES 1–10

The lip side of a bovine anterior tooth was cut to expose a dentin surface, and the dentin surface was polished with #600 emery paper to form an adhesion surface.

The adhesion surface was washed with water and dried, and then a solution containing a metal compound, an acidic monomer and a polymerizable monomer which are shown in Table 1 was applied as a primer. After 10 seconds, the primer was dried by air-blowing it with an air gun, and then an adhesion area was defined by attaching a cellophane tape having a hole having a diameter of 5 mm.

Then, the following solution (curing composition) was applied onto the primer, and the resultant coating of the curing composition was uniformly spread by lightly air-blowing the same. The curing composition had been pre-pared by adding 30 parts by weight of partial oxidate of tributylboron (TBBO, supplied by Sun Medical Co., Ltd) as a polymerization initiator to a mixture comprising 50 parts by weight of methyl methacrylate (supplied by Wako Pure Chemical Industries Ltd., Wako special grade), 30 parts by weight of 2.2-bis[(4-(methacryloxyethoxy)phenyl]propane (NK ester D-2.6E, supplied by Shin-Nakamura Chemical Co., Ltd.), 15 parts by weight of 2-hydroxyethyl methacrylate (supplied by Wako Pure Chemical Industries Ltd., Wako special grade) and 5 parts by weight of 4-methacryloxyethyltrimellitic acid anhydride (supplied by Sun Medical Co., Ltd).

After 30 seconds, a 1 mm thick Teflon mold having a hole with a diameter of 5 mm was attached to the adhesion surface, and this hole portion was filled with a composite resin for dental therapy (Siluxplus, supplied by 3M Co., Ltd.). The composite resin was cured by exposing it to visible light from a visible light irradiation apparatus for dental therapy (Translux supplied by Kulzer) at a distance of 5 mm for 60 seconds.

A PMMA rod was bonded to the cured composite resin through a fast-curable and instantaneous-polymerization resin for dental therapy (Metafast, supplied by Sun Medical Co., Ltd.), to prepare an adhesion test sample. FIG. 1 schematically shows a sample, in which numeral 1 indicates the PMMA rod, numeral 2 indicates the composite resin, numeral 3 indicates the Teflon mold, numeral 4 indicates the cellophane tape, numeral 5 indicates the adhesive layer, and numeral 6 indicates a bovine tooth.

The adhesion test sample was allowed to stand at room temperature for 30 minutes, immersed in distilled water at 37° C. for 24 hours and then subjected to a tensile test to measure an adhesion strength between the PMMA rod and the tooth (dentin). The adhesion strength is an average value from five test samples.

Table 1 shows the results of the above adhesion test.

TABLE 1

| | Primer composition and adhesion strength | | | | |
|---|---|---|---|---|---|
| | Composition (wt. %) | | | | Adhesion strength |
| | Solvent | Metal compound | Acidic monomer | Polymerizable monomer | (MPa) |
| Example 1 | Water: 45 | Ferric nitrate: 0.1 | 4-META: 5 | HEMA: 50 | 18.8 |
| Example 2 | Water: 30 Ethanol: 20 | Ferric nitrate: 0.05 | 4-META: 5 | HEMA: 45 | 17.3 |
| Example 3 | Water: 40 | Ferric nitrate: 0.01 | 4-META: 5 | HEMA: 45 3G: 10 | 15.2 |
| Example 4 | Water: 40 Ethanol: 40 | Ferric nitrate: 0.05 | 4-MASA: 5 | 3G: 15 | 16.6 |
| Example 5 | Water: 45 | Cupric chloride: 0.3 | 4-META: 5 | HEMA: 40 3G: 10 | 13.8 |
| Example 6 | Water: 40 Ethanol: 20 | Cobalt chloride: 0.3 | 4-META: 5 | HEMA: 25 3G: 10 | 11.2 |
| Example 7 | Water: 40 | Ferric sulfate: 0.2 | TBAS: 3 | HEMA: 47 3G: 10 | 17.2 |
| Example 8 | Water: 40 | Ferric sulfate: 0.2 | Phosmer M: 3 | HEMA: 47 3G: 10 | 16.5 |
| Example 9 | Water: 25 Acetone: 25 | Ferric nitrate: 0.05 | 4-META: 5 | HEMA: 35 UDMA: 10 | 18.2 |
| Example 10 | Water: 30 Acetone: 20 | Ferric nitrate: 0.02 | 5-MASA: 5 | HEMA: 30 3G: 10 2E: 5 | 16.2 |

The abbreviations shown in Table 1 stand for the following.

4-META: 4-methacryloxyethyltrimellitic acid anhydride (supplied by Sun Medical Co., Ltd.)

TBAS: 2-acrylamide-2-methylpropanesulfonic acid (supplied by Nittoh Chemical Co., Ltd.)

Phosmer: acid phosphooxyethyl methacrylate (supplied by Unichemical Co., Ltd.)

5-MASA: 5-methacryloylaminosalicylic acid (Mitsui Petrochemical Industries, Ltd., purity of at least 98%).

HEMA: 2-hydroxyethyl methacrylate (supplied by Wako Pure Chemical Industries Ltd., Wako special grade)

3G: triethylene glycol dimethacrylate (NK ester 3G, supplied by Shin-Nakamura Chemical Co., Ltd.)

UDMA: Urethane dimethacrylate (Art Resin SH500S, supplied by Negami Kogyo K.K.)

2E: 2,2-bis[(4-methacryloxypolyethoxy)phenyl]propane (NK ester D-2.6E, supplied by Shin-Nakamura Chemical Co., Ltd.)

Comparative Example 1

A bovine anterior tooth and a PMMA rod were bonded to each other in the same manner as in Example 1 except that no primer was applied (a curing composition was directly applied).

The adhesion strength was 0.8 MPa.

Comparative Examples 2–7

A bovine anterior tooth and a PMMA rod were bonded to each other in the same manner as in Example 1 except that the primer was replaced with a solution shown in Table 2.

Table 2 shows the adhesion strength.

TABLE 2

Primer composition and adhesion strength

| | Composition (wt. %) | | | | Adhesion strength (MPa) |
|---|---|---|---|---|---|
| | Solvent | Metal compound | Acidic monomer | Polymerizable monomer | |
| Comp. Example 2 | Water: 45 | — | 4-META: 5 | HEMA: 50 | 2.8 |
| Comp. Example 3 | Water: 50 | Ferric nitrate: 0.1 | — | HEMA: 50 | 5.8 |
| Comp. Example 4 | Water: 25 Ethanol: 70 | Ferric nitrate: 0.1 | 4-META: 5 | — | 9.5 |
| Comp. Example 5 | Water: 45 | Cupric chloride: 0.3 | — | — | 3.6 |
| Comp. Example 6 | Ethanol: 95 | — | 5-MASA: 5 | — | 1.5 |
| Comp. Example 7 | Water: 70 | — | — | HEMA: 30 | 1.1 |

What is claimed is:

1. A method for adhesion of a material to a tooth surface which comprises applying a primer solution composition comprising (a) at least one metal compound selected from the group consisting of an iron compound, a copper compound and a cobalt compound, (b) a polymerizable acrylic or methacrylic monomer having a carboxyl group or a group convertible to a carboxyl group and (c) a polymerizable monomer having no acidic group and having a (meth)acrylate group, said metal compound (a), said polymerizable monomer (b) and said polymerizable monomer (c) being in a concentration of 0.0001 to 1% by weight, 0.1 to 30% by weight and 70 to 99.9% by weight, respectively, base on the amount of the components (a), (b) and (c), to a tooth surface directly, and applying thereto a curing composition containing trialkylboron or its partial oxidate and a polymerizable monomer and having an adhesion strength of at least 11.2 MPa.

2. The method for adhesion of a material of claim 1, wherein the copper compound is a cupric copper compound.

3. The method for adhesion of a material of claim 1, wherein the polymerizable monomer having no acidic group is a member selected from the group consisting of 2-hydroxyethyl methacrylate and triethylene glycol dimethacrylate and mixtures thereof.

4. A primer solution composition to be applied directly to a tooth surface, (A) which comprises (a) a cupric copper compound, (b) a polymerizable acrylic or methacrylic monomer having a carboxyl group or a group convertible to a carboxyl group and (c) a polymerizable monomer having no acidic group and having a (meth)acrylate group, said metal compound (a), said polymerizable monomer (b) and said polymerizable monomer (c) being in concentration of 0.0001 to 1% by weight, 0.1 to 30% by weight and 70 to 99.9% by weight, respectively, based on the weight of the components (a), (b) and (c), and (B) which has adhesion properties to a tooth surface to obtain an adhesion strength of at least 11.2 MPa.

5. The primer solution of claim 4, which further comprises a solvent selected from the group consisting of water, an organic solvent and mixtures thereof.

6. A primer solution composition to be applied directly to a tooth surface, (A) which comprises (a) at least one metal compound selected from the group consisting of an iron compound, a copper compound and a cobalt compound, (b) a polymerizable monomer having an acidic group which is a member selected from the group consisting of 4-methacryloxyethyltrimellitic acid anhydride, 4-methacryloylaminosalicylic acid, 5-methacryloylaminosalicylic acid, 2-acrylamide-2-methylpropanesulfonic acid, acid phosphooxyethyl methacrylate and mixtures thereof, and (c) a polymerizable monomer having no acidic group and having a (meth)acrylate group which is a member selected from the group consisting of 2-hydroxyethyl methacrylate, triethylene glycol dimethacrylate, urethane dimethacrylate, 2,2-bis((4-methacryloxypolyethoxy)phenyl)propane and mixtures thereof, said metal compound (a), and said polymerizable monomer (b) and said polymerizable monomer (c) being in a concentration of 0.0001 to 1% by weight, 0.1 to 30% by weight and 70 to 99.9% by weight, respectively, based on the weight of the components (a), (b) and (c), and (B) which has adhesion properties to a tooth surface to obtain an adhesion strength of at least 11.2 MPa.

7. The primer solution of claim 6, which further comprises a solvent selected from the group consisting of water, an organic solvent and mixtures thereof.

8. The primer solution of claim 6, wherein the copper compound is a cupric copper compound.

9. A method for adhesion of a material to a tooth surface which comprises applying a primer solution composition comprising (a) at least one metal compound selected from the group consisting of an iron compound, a copper compound and a cobalt compound, (b) a polymerizable acrylic or methacrylic monomer having at least one acidic group selected from the group consisting of a carboxyl group, a sulfonic acid group and phosphoric group, and (c) a polymerizable monomer having no acidic group and having a (meth)acrylate group, said metal compound (a), said polymerizable monomer (b) and said polymerizable monomer (c) being in a concentration of 0.0001 to 1% by weight, 0.1 to 30% by weight and 70 to 99.9% by weight, respectively, based on the weight of the components (a), (b), and (c), to a tooth surface directly, and applying thereto a curing composition containing trialkylboron or its partial oxidate and a polymerizable monomer and having an adhesion strength of at least 11.2 MPa.

10. The method of claim 9, wherein the primer solution further comprises a solvent selected from the group consisting of water, an organic solvent and mixtures thereof.

11. The method of claim 9, wherein in primer solution the copper compound is a cupric copper compound.

12. A primer solution composition to be applied directly to a tooth surface, (A) which comprises (a) at least one metal compound selected from the group consisting of an iron compound, a copper compound and a cobalt compound, (b) a polymerizable acrylic or methacrylic monomer having a carboxyl group or an group convertible to a carboxyl group and (c) a polymerizable monomer having no acidic group and having a (meth)acrylate group, said metal compound (a), said polymerizable monomer (b) and said polymerizable monomer (c) being in concentration of 0.01 to 0.3% by weight, 3 to 5% by weight and 15 to 57% by weight, respectively, and (d) 40 to 80% by weight of a solvent selected from the group consisting of water, an organic solvent and mixtures thereof, based on the weight of the components (a), (b), (c) and (d), and (B) which has adhesion properties to a tooth surface and an adhesion strength of at least 11.2 MPa.

13. The primer solution of claim 12, wherein the copper compound is a cupric copper compound.

14. The primer solution of claim 12, wherein the polymerizable monomer having no acidic group is a member selected from the group consisting of 2-hydroxyethyl methacrylate, triethylene glycol dimethacrylate, urethane dimethacrylate, 2,2 -bis((4-methacryloxy-polyethoxy)phenyl)propane and mixtures thereof.

15. A primer solution composition to be applied directly to a tooth surface, (A) which comprises (a) at least one metal compound selected from the group consisting of an iron compound, a copper compound and a cobalt compound, (b) a polymerizable monomer having an acidic group which is a member selected from the group consisting of 4-methacryloxyethyltrimellitic acid anhydride, 4-methacryloylaminosalicylic acid, 5-methacryloylaminosalicylic acid, 2-acrylamide-2-methylpropanesulfonic acid, acid phosphooxyethyl methacrylate and mixtures thereof, and (c) a polymerizable monomer having no acidic group and having a (meth)acrylate group which is a member selected from the group consisting of 2-hydroxyethyl methacrylate, triethylene glycol dimethacrylate, urethane dimethacrylate, 2,2-bis((4-methacryloxypolyethoxy)phenyl)propane and mixtures thereof, said metal compound (a), and said polymerizable monomer (b) and said polymerizable monomer (c) being in a concentration of 0.01 to 0.3% by weight, 3 to 5% by weight and 15 to 57% by weight, respectively, and (d) 40 to 80% by weight of a solvent selected from the group consisting of water, an organic solvent and mixtures thereof, based on the weight of the components (a), (b), (c) and (d), and (B) which has adhesion properties to a tooth surface and an adhesion strength of at least 11.2 MPa.

16. The primer solution of claim 15, wherein the copper compound is a cupric copper compound.

17. A method for adhesion of a material to a tooth surface which comprises applying a primer solution composition comprising (a) at least one metal compound selected from the group consisting of an iron compound, a copper compound and a cobalt compound, (b) a polymerizable acrylic or methacrylic monomer having at least one acidic group selected from the group consisting of a carboxyl group, a sulfonic group and phosphoric group, and (c) a polymerizable monomer having no acidic group and having a (meth)acrylate group, said metal compound (a), said polymerizable monomer (b) and said polymerizable monomer (c) being in a concentration of 0.01 to 0.3% by weight, 3 to 5% by weight, and 15 to 57% by weight, respectively, and (d) 40 to 80% by weight of a solvent selected from the group consisting of water, an organic solvent and mixtures thereof, based on the weight of the components (a), (b), (c) and (d), to a tooth surface directly, and applying thereto a curing composition containing trialkylboron or its partial oxidate and a polymerizable monomer and having an adhesion strength of at least 11.2 MPa.

18. The method of claim 17, wherein in the primer solution the copper compound is a cupric copper compound.

19. A primer solution composition to be applied directly to a tooth surface, (A) which comprises (a) at least one metal compound selected from the group consisting of an iron compound, a copper compound and a cobalt compound, (b) a polymerizable acrylic or methacrylic monomer having a carboxyl group or a group convertable to a carboxyl group and (c) a polymerizable monomer having no acidic group and having a (meth)acrylate group, wherein the polymerizable monomer having no acidic group is a member selected from the group consisting of 2-hydroxyethyl methacrylate, triethylene glycol dimethacrylate, urethane dimethacrylate, 2,2-bis((4-methacryloxy-polyethoxy)phenyl)propane and mixtures thereof, and said metal compound (a), said polymerizable monomer (b) and said polymerizable monomer (c) being in concentration of 0.001 to 1% by weight, 0.1 to 30% by weight and 70 to 99.9% by weight, respectively, based on the weight of the components (a), (b) and (c), and (B) which has adhesion properties to a tooth surface to obtain an adhesion strength of at least 11.2 MPa.

20. The primer solution of claim 19, which further comprises a solvent selected from the group consisting of water, an organic solvent and mixtures thereof.

21. The primer solution of claim 19, wherein the copper compound is a cupric copper compound.

* * * * *